United States Patent
Kao

(10) Patent No.: US 7,612,049 B2
(45) Date of Patent: Nov. 3, 2009

(54) METHOD OF INHIBITION THE GROWTH OF ALGAE

(75) Inventor: Chih-Ta Kao, Jhong Li (TW)

(73) Assignee: ITEQ Corporation, Ping Chen, Taoyuan (TW)

( * ) Notice: Subject to any disclaimer, the term of this patent is extended or adjusted under 35 U.S.C. 154(b) by 97 days.

(21) Appl. No.: 11/936,892

(22) Filed: Nov. 8, 2007

(65) Prior Publication Data

US 2009/0124575 A1 May 14, 2009

(51) Int. Cl.
*A01N 43/16* (2006.01)
(52) U.S. Cl. .......................... 514/62; 536/17.2
(58) Field of Classification Search ........... 514/62; 536/17.2
See application file for complete search history.

(56) References Cited

OTHER PUBLICATIONS

David M. Carlberg, Cleanroom Microbiology for the Non-Microbiologist, Boca Raton CRC Press, Second Edition, 2005, pertinent pp. 21-22.*
Alan W. White, Moshe Shilo, Heterotophic Growth of the Filamentous Blue-Green Alga *Plectonema boryanum*, Arc. Microbiol. 1975, vol. 102, pp. 123-127.*
Hector R. Bravo, Waldo Lazo, Antialgal and Antifungal Activity of Natural Hydroxyamic Acids and Related Compounds, J. Agric. Food Chem. 1996, vol. 44, issue 6, pp. 1569-1571.*
Feng-Min Li, Hong-Ying Hu, Isolation and Characterization of a Novel Antialgal Allelochemical from *Phragmites communis*, Appl. Environ. Microbiol. 2003, vol. 71, issue 11, pp. 6545-6553.*
T. Berman, S. Chava, Algal Growth on Organic Compounds as Nitrogen Sources, J. Planton Res. 1999, vol. 21, 1423-1437.*
Thierry Lebeau, Jean-Michael Robert, Diatom Cultivation and Biotechnologically Relevant Products. Part I: Cultivation at Various Scales, Appl. Microbiol. Biotechnol. 2003, vol. 60, pp. 612-623.*
Jankevicius, K. And Budriene, S. and Baranauskiene, A. and Jankaviciute, G., Lietuvos TSR Mokslu Akademijos Darbai, Serija C: Biologijos Mokslai, Effect of N-acetyl-D-glucosamine on the development and amino acid composition of plankton algae under various temperature conditions, vol. 4, pp. 7-14 (1982).*

* cited by examiner

*Primary Examiner*—Shaojia Anna Jiang
*Assistant Examiner*—Bahar Schmidtmann
(74) *Attorney, Agent, or Firm*—Thomas, Kayden, Horstemeyer & Risley

(57) ABSTRACT

The inhibition of Chlorophyta growth in water needed to be treated can be accomplished by the addition of about 100 ppm glucosamine. The inhibition of *Microcystic aeruginosa* and *Microcystis flos-aquae* growth in water needed to be treated can be accomplished by the addition of about 10 to 50 ppm glucosamine. The addition of glucosamine to water needed to be treated, such as reservoirs, offers an environmentally safe method for inhibiting algae growth.

2 Claims, No Drawings

METHOD OF INHIBITION THE GROWTH OF ALGAE

BACKGROUND

1. Field of Invention

The present invention relates to water treatment. More particularly, the present invention relates to growth inhibition of algae in water.

2. Description of Related Art

Many reservoirs around the world have water quality problems and one of the problems is nutrient pollution. Nutrient pollution comes from many sources, including fertilizer run off from farms, livestock waste and inadequately treated sewage. Excessive nutrients such as nitrogen and phosphorus contribute algae matter in our water supplies.

Algae blooms can have a significant environmental impact due to the decrease in oxygen in the water, resulting in the die-off of fish and other organisms. Moreover, when disinfectants, such as chlorine, are added to drinking water supplies, chlorine combines with some algae to form disinfection by-products, trihalomethane. Trihalomethanes and other disinfection by-products found in the tap water have been linked to cancer and birth defects. Furthermore, these algal blooms can produce significant quantities of natural toxins. Some algae, especially Cyanobacteria, produce either hepatotoxin or neurotoxin or even both. These toxins can cause severe dermatitis through skin contact, as well as gastrointestinal inflammation with oral exposure. Singly or in mixtures, these Cyanobacterial neurotoxins can cause death within minutes secondary to respiratory paralysis. At lower doses of hepatotoxin, enteritis and hepatitis are seen shortly after ingestion of these toxins.

In the conventional way, copper sulfate is probably the most widely used chemical application for controlling algae in water suppliers throughout the world. However, like other heavy-impact pollutants, copper accumulates in higher and higher concentrations as it moves up the food chain, and eventually leads to declines in fish and frog populations, according to several scientific studies. Short-term exposure to copper can lead to gastrointestinal distress, and long-term exposure causes liver or kidney damage. For the forgoing reasons, there is a need for inhibiting the growth of algae.

SUMMARY

The present invention is directed to a method that inhibits the growth of algae without being hazard to human's health or the environment.

In one aspect, the present invention provides a method for inhibiting the growth of algae which comprises adding glucosamine into water needed to be treated.

According to one embodiment of the invention, the algae inhibited by glucosamine is Chlorophyta, Cyanobacteria or the combination thereof. The concentration of the added glucosamine in the treated water is at least 10 ppm/mg algae.

In another aspect, the present invention provides a method for inhibiting the growth of algae. This method comprises adding a monocyclic compound into water needed to be treated wherein the monocyclic compound comprises a hexose and at least one amine group substituting at least one hydroxy group of the hexose at C1, C3 and/or C4 position.

In conclusion, glucosamine greatly inhibits algal growth. In addition, since glucosamine is a natural degradable and eatable compound, it will not accumulate in the environment or be hazardous for human health after being used for a long time.

It is to be understood that both the foregoing general description and the following detailed description are by examples, and are intended to provide further explanation of the invention as claimed.

DESCRIPTION OF THE EMBODIMENTS

Reference will now be made in detail to the present embodiments of the invention, examples of which are illustrated in the accompanying drawings. Wherever possible, the same reference numbers are used in the drawings and the description to refer to the same or like parts.

Embodiment I

In order to test if glucosamine inhibited the growth of algae or not, in the following embodiment, glucosamine was added to samples and then observed. Moreover, since chlorophyll-a content of algae is widely used as an indicator of the quality of freshwater bodies and the abundance of algae, the chlorophyll-a content in the sample was detected by spectrometry.

First, two 20 ml portions of water were obtained from a fishpond which contains a varieties of algae and is especially abundant in Chlorophyta. Both portions of water were labeled as control and sample I respectively. Next, 100 ppm glucosamine was added in sample I, and then the control and sample I were cultured for 28 days with Bold's medium. After 28 days later, it was found that the algae in the control bloomed, but not sample I. In order to determine the algae content in both solutions, the chlorophyll-a content examination was provided as follows.

The solution of the control and sample I were centrifuged at 10000 rpm at 20° C. for 3 hours, and then the supernatant were poured out. Next, two 10 ml portions of 95% (v/v) ethanol were added to sample I and the control and mixed with the residues. Next, the solution of sample I and the control were water-bathed in 60° C. water for 30 mins to extract Chlorophyll-a. When being bathed in the water, the solution of the control and sample I were shaken every ten minutes. After that, the solutions were centrifuged at 5000 G at 20° C. for 15 minutes and the supernatants were kept. Then, the absorbance at 665 nm of the control and sample I were detected. Finally, according to the "*Standard Methods for the Examination Chlorophyll-a in Water-Ethanol Extraction*" issued by National Indian Education Association, Taiwan (NIEA E508.00B), the absorbance at 665 nm of the control and sample I were calibrated and the concentration of Chlorophyll-a content can be calculated by the absorbance measure.

According to the method above, the concentration of Chlorophyll-a content in sample I and the control calculated were 74 ppb and 652 ppb respectively. Compared with the control, the low Chlorophyll-a content in sample I shows that the growth of algae is inhibited by glucosamine. The testing result above further indicates that the growth of Chlorophyta in sample I was inhibited by glucosamine because sample I was acquired from the fishpond abundant in Chlorophyta which contributed the major Chlorophyll-a content.

Embodiment II

To verify whether Cyanobacteria can be inhibited by glucosamine or not, in the following embodiment, two kinds of toxic Cyanobacteria, *Microcystis aeruginosa* and *Microcystis aeruginosa*, were examined. The detailed procedures are described below.

First, four 50 ml portions of water with *Microcystis aeruginosa* were obtained and labeled as control and sample II, sample III, and sample IV respectively. The weight concentration of *Microcystis aeruginosa* cell in these four samples 883 μg/L (ppb). Next, different amount of glucosamine was added into the three samples so that the concentrations of glucosamine in samples II, III, and IV were 10 ppm, 20 ppm, and 50 ppm, respectively. After that, the control and sample II, III, and IV were cultured for 14 days with Bold's medium, and the Chlorophyll-a content of each sample were detected every 7 days. The procedures of detecting Chlorophyll-a content was the same as mentioned in embodiment I and the whole process was repeated for testing *Microcystis flos-aquae*. The testing results of *Microcystis aeruginosa* and *Microcystis flos-aquae* are shown in the following Table I.

TABLE I detection of Chlorophyll-a content

*Microcystis aeruginosa*

| Sample labeled | Control | Sample II | Sample III | Sample IV |
|---|---|---|---|---|
| Concentration of Glucosamine (ppm) | 0 | 10 | 20 | 50 |
| Chlorophyll-a content (ppb) 7$^{th}$ day | 270 | 80 | 65 | 41 |
| Chlorophyll-a content (ppb) 14$^{th}$ day | 2657 | 1922 | 1004 | 72.3 |
| Inhibition efficiency (after 14 days) | — | 27.6% | 62.2% | 97.2% |

*Microcystis flos-aquae*

| Sample labeled | Control | Sample V | Sample VI | Sample VII |
|---|---|---|---|---|
| Concentration of Glucosamine (ppm) | 0 | 10 | 20 | 50 |
| Chlorophyll-a content (ppb) 7$^{th}$ day | 178 | 0 | 3 | 15 |
| Chlorophyll-a content (ppb) 14$^{th}$ day | 438 | 225 | 142 | 92 |
| Inhibition efficiency (after 14 days) | — | 48.6% | 67.5% | 78.9% |

* the original chlorophyll-a content of *Microcystis aeruginosa* and *Microcystis flos-aquae* at the first day were 26.5 ppb and 26.4 ppb.

According to Table 1, it shows that the growth of Cyanobacteria was inhibited by glucosamine. Taking *Microcystis aeruginosa* for example, the chlorophyll-a content in the control without any glucosamine added was 270 ppb and 2657 ppb at the 7$^{th}$ day and the 14$^{th}$ day respectively. However, by adding glucosamine, the chlorophyll-a content in samples II, III, and IV were obviously reduced under the same culturing condition. The chlorophyll-a content in Sample II was 80 ppb at the 7$^{th}$ day and 1922 ppb at the 14$^{th}$ day when the concentration of glucosamine was 10 ppm. For sample III which contains 20 ppm of glucosamine, the concentration of chlorophyll-a was much less than that of sample II. For sample IV, the chlorophyll-a content reduced the most. It was only 41 ppb at the 7$^{th}$ day and 72.3 ppb at the 14$^{th}$ day. In view of the above, even though the concentration of glucosamine was only 10 ppm in sample II, the inhibition ability to algae has been demonstrated. Furthermore, the inhibition efficiency of each sample were also calculated and listed in Table I. According to Table I, the inhibition efficiency to *Microcystis aeruginosa* after 14 days was from 27.6% to 97.2% as the concentration of glucosamine was increased from 10 ppm to 50 ppm. Glucosamine also demonstrated great inhibition to *Microcystis flos-aquae*. As shown in Table I, the inhibition efficiency increased from 48.6% to 78.9% as the concentration of glucosamine went up.

However, the amount of inhibitor needed for inhibiting the growth of algae should based on the water quality or the amount of algae in the treated water, instead of only considering the volume of water. Hence, in the embodiment of the present invention, the minimum effective amount of glucosamine needed is also calculated on basis of the weight concentration of Cyanobacteria in water. As mentioned above, the weight concentration of Cyanobacteria was 883 1μg/L which equals to 0.883 mg/L. Furthermore, according to Table I, 10 ppm of glucosamine in water can provide inhibition ability. Therefore, the minimum effective amount of glucosamine is about at least 10 ppm/mg algae (i.e. 10 ppm is divided by 0.883 mg). In other words, when 1L of water contains 0.883 mg of algae, about 10 mg of glucosamine should be added.

In view of the above, the growth of algae (i.e. Chlorophyta and Cyanobacteria) can be inhibited by glucosamine. The more glusosamine added, the better inhibition efficiency provided. Moreover, being a naturally degradable and eatable compound, glucosamine not only inhibits the algal growth substantially but is not harmful to the environment or human' health even after long-term usage.

Although the present invention has been described in considerable detail with reference and certain embodiments thereof, other embodiments are possible. Therefore, their spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A method for inhibiting the growth of Chlorophyta, comprising adding glucosamine into water needed to be treated, in which the added glucosamine has a concentration in the treated water of about 100 ppm.

2. A method for inhibiting the growth of *Microcystic aeruginosa* and *Microcystis flos-aquae*, comprising adding glucosamine into water needed to be treated, in which the added glucosamine has a concentration in the treated water from about 10 to 50 ppm.

* * * * *